United States Patent [19]

Lawrence, Jr. deceased et al.

[11] Patent Number: 4,477,778

[45] Date of Patent: Oct. 16, 1984

[54] HYDROGEN DETECTOR

[75] Inventors: Samuel C. Lawrence, Jr. deceased, late of Seattle, Wash.; by Julia F. Lawrence executrix, 16414 Maplewild Ave. SW., Seattle, Wash. 98166; Gary M. Lawrenson, King County, Wash.

[73] Assignees: Lawrence Electronics Co.; Julia F. Lawrence, both of Seattle, Wash. ; a part interest

[21] Appl. No.: 357,865

[22] Filed: Mar. 15, 1982

[51] Int. Cl.$^3$ ............................................. G01N 27/62
[52] U.S. Cl. ................................................... 324/466
[58] Field of Search ........................ 324/466, 464, 468

[56] References Cited

U.S. PATENT DOCUMENTS 3,241,056  3/1966  Lawrence, Jr. ...................... 324/466
3,280,619  10/1966  Spies ..................................... 324/466

Primary Examiner—Michael J. Tokar
Assistant Examiner—Kevin D. O'Shea
Attorney, Agent, or Firm—Seed and Berry

[57] ABSTRACT

A hydrogen detector having a hydrogen-permeable membrane between the atmosphere and the inside of a vacuum tube is heated by an adjacent filament located within the tube.

5 Claims, 4 Drawing Figures

HYDROGEN DETECTOR

DESCRIPTION

1. Technical Field

The present invention relates to hydrogen detectors of the type using a vacuum tube probe with a hydrogen-permeable membrane and an internal hydrogen ionizer.

2. Background Art

The use of modified radio vacuum tubes, such as 6V6 tubes, in hydrogen ion gauges is well known in the hydrogen detector art. The tube, acting as a sensor or probe, measures the hydrogen pressure buildup in the tube arising from diffusion through the shell (envelope) of the tube by ionizing the internally desorbed hydrogen molecules with a beam of electrons emitted by a filament-heated cathode. The hydrogen ions so formed are collected on a negatively charged ion plate, and this creates an electric current on the plate that is proportional to the hydrogen pressure in the tube. As disclosed in U.S. Pat. No. 3,258,683, sensitivity is improved by limiting the amount of shell area which is hydrogen permeable to provide diffusion "windows" (membranes), these preferably being located opposite portions of the shell which are free of gettering material, commonly barium. In the devices disclosed in U.S. Pat. No. 3,258,683, the vacuum tubes had steel shells and the hydrogen-permeable windows were created by covering all of the external shell area other than the window with a hydrogen-impermeable coating.

It has also been known in the art that a palladium/silver alloy, preferably 75% palladium and 25% silver, was a superior material for hydrogen diffusion because of the high hydrogen-absorbing power of palladium. In 1972, the Naval Air Development Center at Worminster, Pa., conducted tests with corrosion detection gauges utilizing vacuum tube probes of the type disclosed in U.S. Pat. No. 3,258,683 and a modified such probe, designated CDG-2, also developed at Lawrence Electronics Co., Seattle, Wash., in which the hydrogen-permeable window comprised a palladium/silver, hollow, needle-like extension of the vacuum tube shell approximately 1¼ inch long and having a diameter of 1/16 inch. The results of these tests were published in Report No. NADC-72251-VT, dated Dec. 5, 1972. In using such a probe with a palladium/silver membrane tip, or with a diffusion window such as shown in Pat. No. 3,258,683, it is important to have the membrane heated to about 150° C. to 250° C. to speed up the hydrogen diffusion. Prior to the present invention, this heating was done externally.

External heating of the hydrogen diffusion membrane is difficult to accurately control, is inconvenient, and may increase contamination risk. An important use of a hydrogen detection probe is in conjunction with a test chamber for measuring residual hydrogen in small metal specimens or for measuring hydrogen corrosion in a tank or pipe to the outer wall of which the test chamber has a sealed connection. In either instance, the test chamber must be free of contaminants, and this is accomplished by purging the chamber with a highly purified inert gas, such as argon. Since the diffusion membrane is located within the test chamber, either the entire test chamber must be heated to heat the membrane, or a heater must be inserted in the test chamber adjacent the membrane. It is also preferred to heat the test specimen to accelerate hydrogen effusion therefrom. If the specimen is a small metal part, it is preferred to induction heat the specimen, commonly to about 1100° C. If the specimen is the wall of a tank or pipe, and corrosion is being monitored, the specimen temperature may only need to be about 20° C. However, even this may require heating of the specimen, in which case, heat must be concentrated on the specimen, normally from a heat source located within the test chamber. This makes it increasingly difficult to closely control the temperature of the diffusion membrane. Furthermore, when testing of a pipe or other specimen is being done in the "field," the less heating apparatus to contend with, the better.

Accuracy of hydrogen readings respecting a specimen is effected by the heat of the diffusion membrane and the specimen. It is particularly important during corrosion monitoring conducted for several days or weeks that the desired temperatures be able to be maintained and monitored.

Heating of the membrane is not only necessary for hydrogen detection, it is also necessary to heat the membrane between tests to out-gas the hydrogen. It is preferred to be able to accomplish the out-gassing without having to remove the probe from its seat in the chamber wall. It is also preferred to heat the membrane from the same source during the test cycle and the out-gassing.

Disclosure of Invention

Accordingly, the present invention aims to provide a simplified, accurate, easily controlled means for heating the hydrogen diffusion membrane which can be used conveniently under a great variety of test conditions, locations and environments.

In carrying out the invention, the shell of a vacuum tube is preferably made of glass to be hydrogen impermeable and has one end necked and sealed around the root end of a projecting palladium/silver tube closed at the tip to serve as a hydrogen diffusion membrane. The other end of the tube is closed by a glass, pronged base. Two of the base prongs are connected by leads to a heating filament located within the tubular membrane. Other of the prongs are connected to the cathode heater filament, cathode, grids and plate of a standard 6V6 tube unit mounted in the shell. Suitable gettering is provided. A socket adapted to receive the prongs of the pronged base are connected to a suitable power and control circuit.

BEST MODE FOR CARRYING OUT THE INVENTION

Figure 1:
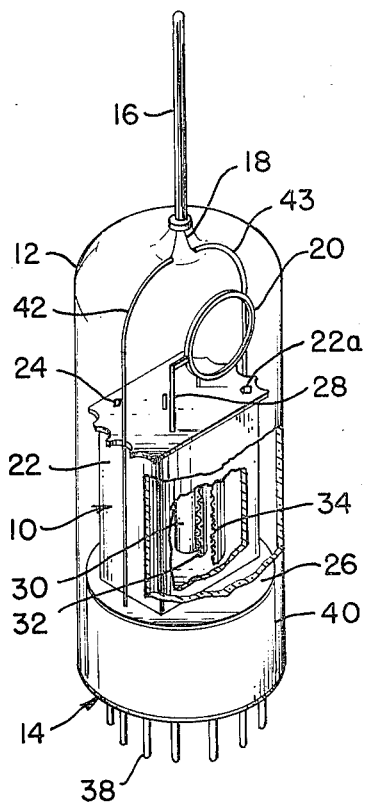
FIG. 1 is a perspective view illustrating a typical probe embodying the invention, part of the shell plate and grids being broken away.

Referring to the drawings, it is seen that an ionizer and collector unit 10, which may be that of a standard 6V6 tube, is mounted in a round glass shell 12, closed at one end by a pronged insulating base assembly 14 and necked at its other end to seal around the root end of a hollow, needle-like, hydrogen-permeable membrane 16 closed at its tip end and exposed to the interior of the shell 12. The material of the membrane 16 is preferably an alloy having 75% palladium and 25% silver. Extending substantially the full length of the membrane 16 is a resistance heating wire 18. Also provided within the shell 12 is a suitable getter, which may initially be stored on a carrier ring 20 for later vaporization by induction heating of the ring.

The unit 10 typically has a tubular plate 22 (collector) of generally oblong cross-section on the outside, with top and bottom mica cover sheets 24,26 extending outwardly therebeyond. Part of the ends of the plate 22 is cut back to provide ports. The cover sheets are held in place by tab extensions 22a of the plate 22 extending through openings therein and bent over. A wire arm 28 is welded to one of these tabs 22a to support the carrier ring 20. This ring has a generally U-shaped cross-section, with the mouth aimed toward the shell 12 so that when the ring is induction heated after assembly and evacuation of the probe, gettering (such as barium) stored in the ring cavity will deposit as a coating on an adjacent portion of the inner face of the shell and not within the membrane 16.

Mounted concentrically within the plate 22 are a cathode 30 and inner and outer grids 32,34 of wire screen. Within the cathode 30 is a heater filament 36. The outer grid 34 functions as an accelerator electrode and the inner grid 32 is employed for regulating the electron current formed within the probe under standard conditions. The plate 22 has a negative charge and functions as a hydrogen ion collector.

The base assembly 14 has a typical radio tube construction and comprises a glass disc with wire conductor prongs 38 extending therethrough in sealed relation and arranged in a circular pattern, a standard twelve-prong base being convenient for use. The prongs project upwardly through the base and six of them connect to the plate 22, grids 32 and 34, cathode 30, and heater filament 36 by leads hidden from view in FIG. 1 by a cylindrical skirt 40.

Two other of the prongs 38 project through the bottom cover outwardly of the collector and are connected to a pair of relatively stiff leads 42,43 for the heater filament 18 for the membrane 16. The remaining prongs may be used for support of the bottom micra disc 26 or snipped off above the base plate 14.

Figure 2:
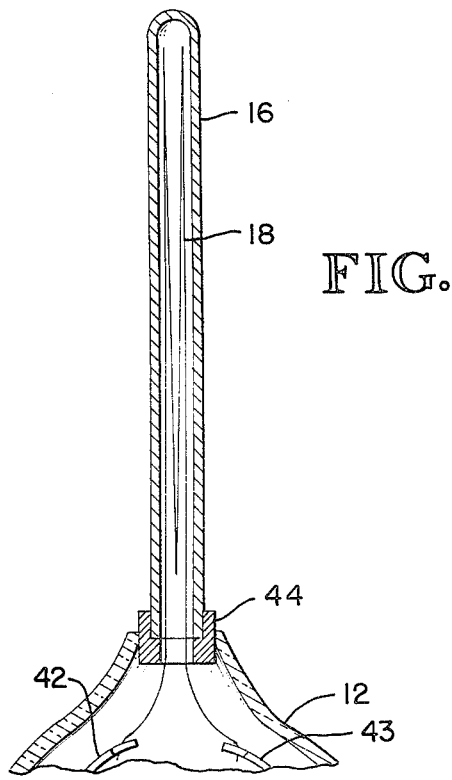
FIG. 2 is a detailed cross-sectional view to an enlarged scale of the membrane tip of the probe.

As shown in FIG. 2, the root end of the membrane 16 is fitted with a collar 44, preferably of a material such as platinum, matched closely as to coefficient of expansion with the glass of the shell 12. The collar 44 is bonded to the membrane by brazing or suitable high-temperature adhesive. When the glass shell 12 is initially blown it is formed with a neck larger in diameter than the collar 44. The outer surface of the collar is oxidized and then fitted into the neck of the shell, whereupon the neck is heated and shrunk against the collar. The oxide surface of the collar becomes bonded to the glass by this procedure.

After the prongs 38 of the plug unit 14 have been connected to the rest of the internal assembly of the probe, including the leads 42,43 and the latter have been suitably connected to the membrane heater filament 18, the entire resulting assembly, with the gettering ring 20 in place, is inserted into the shell 12, with the filament 18 projecting into the membrane 16. Then the glass of the base 14 is fused to the glass of the shell 12. Lastly, the tube is heated and evacuated through a hole in the base 14, which is then sealed. The gettering ring 20 is then induction heated to vaporize the gettering, which deposits in the inside face of the shell adjacent the ring.

Figure 3:
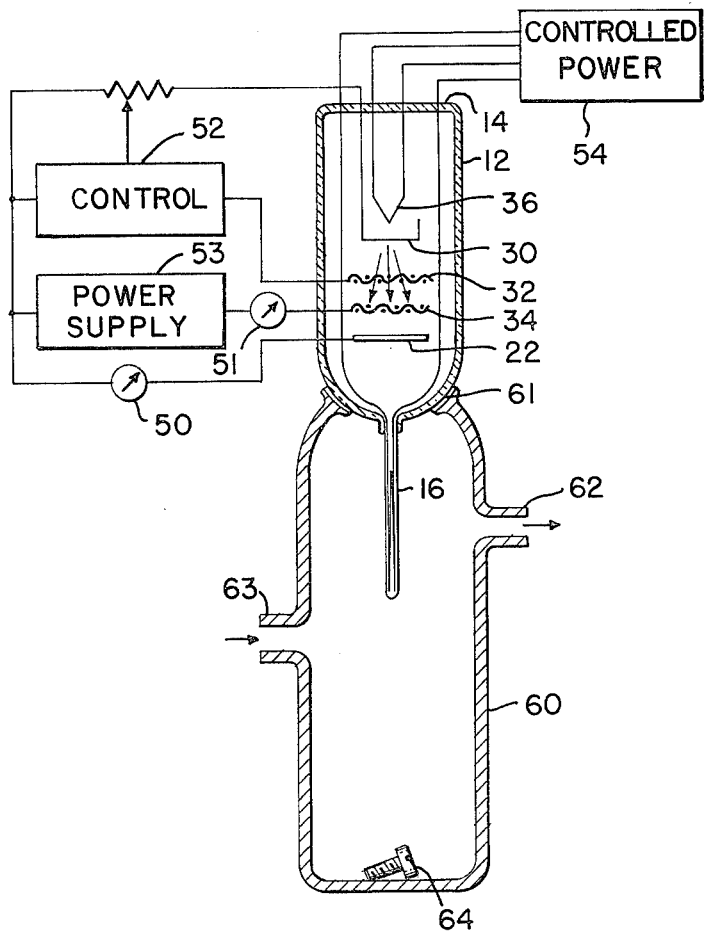
FIG. 3 is a schematic showing the control circuit for the probe and illustrating the probe in use with a test chamber (shown in cross-section) containing a fastening specimen.

A socket matched to the pattern of the prongs 38 is wired, as shown schematically in FIG. 3, to form a measuring circuit. This circuit includes a micro-microammeter 50 for measuring a characteristic of the probe that depends upon the amount of hydrogen that has moved through the membrane 16 into the shell 12, and a milli-ammeter 51 that is used for standardizing the electron emission of the cathode 30. The cathode 30 is connected to one end of a potentiometer, the other end of which is connected to the negative terminal of a power supply 53. The inner grid 32 is connected to the slide wire of the potentiometer 52, and the outer grid is connected via meter 51 to the positive terminal of the power supply 53. The collector 22 is connected through meter 50 the negative terminal of the power supply 53. The voltage supplied by the power supply 53 is of such a magnitude that electrons accelerated from the cathode 30 toward the collector 22 attain energies corresponding to those above the ionization potential of molecular hydrogen.

A power source 54, with suitable respective controls, is connected to the cathode heater filament 36 and the membrane heater filament 18 so that the heat of each can be individually controlled as desired.

As indicated in FIG. 3, a test chamber 60 may be provided, on the upper end of which the probe is seated at 61 in sealed relation, with the membrane 16 projecting into the chamber. The atmosphere, of the chamber is purged of air through exit port 62 by purified argon or other suitable inert gas introduced through port 63. Suitable valving is provided. A specimen, such as, for example, a cleaned bolt 64, is induction heated in the chamber to about 1100° C. to release its hydrogen, which then diffuses through the membrane 16 into the probe.

The electron current flowing between the electron emitter 30 and the electron collector 22 ionizes the hydrogen molecules into H+ atoms. The H+ atoms are attracted to the collector. This generates an electric current proportional to the hydrogen pressure. This current is measured by the gauge 50. Comparison is made with a calibration reading to determine the exact amount of hydrogen present.

The test specimen is removed, and the probe is electrically heated and out-gassed while the chamber is being purged by introducing a current from the cathode 30 to the plate 22 and energizing the filament 18 to heat the membrane 16. The chamber is then ready for the next specimen.

Figure 4:
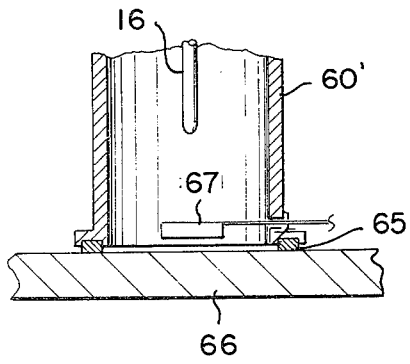
FIG. 4 illustrates use when the test chamber is mounted on a specimen for corrosion monitoring.

As indicated in FIG. 4, a test chamber 60' having an open lower end may be used, with a sealing gasket 65 bearing against a specimen 66, such as an iron pipeline or tank. A heater 67 may be provided to maintain the test zone of the specimen in the chamber at a preferred temperature of, for example, about 20° C. to 100° C. Suitable clamping means is employed to hold the chamber 60' in position. The hydrogen emitted from the test zone of the specimen diffuses through the membrane and is monitored as described before.

As previously indicated, it is preferred that the membrane be 75% palladium and 25% silver. However, other ratios can be used. The membrane is thin walled and can be about 1/16 inch in diameter. The length can be about 1 to 1½ inch long. However, other sizes can be used. Also, the membrane need not be a straight tube or of constant diameter. In some applications, the membrane need not be a tubular extension, the important thing being that it is heated from within the probe by an adjacent heater element.

We claim:

1. A detector for a given gas, comprising:
   a glass vacuum shell having most of its area not permeable as to said gas;
   a palladium alloy membrane which is permeable as to said gas, said membrane being a tubular extension of said shell and connected thereto via a platinum collar on the root end of the membrane;
   a heater element in said shell adjacent said membrane for heating the membrane; and
   ionizing and ion collecting means for said gas in the shell.

2. A detector according to claim 1 in which circuit means is provided external to the shell and is connected to said heater element and ionizing and ion collecting means for energizing the heater element and ionizing means and measuring the current generated in the ion collecting means by the ionized gas.

3. A detector according to claim 1 in which said heater element is located within said tubular extension.

4. A detector according to claim 1 in which said shell has a pronged glass base with outwardly projecting prongs connected within the shell to said heater element and said ionizing and collecting means.

5. A detector according to claim 1 in which the outer surface of said collar is oxidized.

* * * * *